United States Patent [19]

Kallies et al.

[11] Patent Number: 4,748,114
[45] Date of Patent: May 31, 1988

[54] TEST STRIP FOR COLLECTING OF BLOOD SUGAR DAILY PROFILES AND PROCESS FOR ITS PREPARATION

[75] Inventors: Karl-Heinz Kallies, Sebnitz; Dieter Plaschnick, Wolfen; Peter Mohr, Hohen-Neuendorf; Hans-Jürgen Thiele, Dresden; Conrad J. Pahlitzsch, Seibnitz; Lothar Kretschmer, Langburkersdorf; Gert Kallies, Seibnitz, all of German Democratic Rep.

[73] Assignee: VEB Arzneimittelwrk Dresden, Radebeul, German Democratic Rep.

[21] Appl. No.: 703,234

[22] Filed: Feb. 19, 1985

[30] Foreign Application Priority Data

Apr. 9, 1984 [DD] German Democratic Rep. ... 261762

[51] Int. Cl.$^4$ .......... C12Q 1/54; C12Q 1/26; C12N 11/02; C12N 9/96
[52] U.S. Cl. .......... 435/14; 435/25; 435/28; 435/177; 435/178; 435/188; 435/190; 435/192; 435/288; 435/805; 422/56; 422/57
[58] Field of Search .......... 435/14, 28, 25, 190, 435/192, 177, 178, 805, 288, 291, 188; 422/56, 57; 427/2

[56] References Cited

U.S. PATENT DOCUMENTS 3,964,974  7/1976  Banauch et al. .......... 435/4
4,331,761  5/1982  Dawson et al. .......... 435/188
4,543,338  9/1985  Chen .......... 422/56

OTHER PUBLICATIONS

The Merck Index, 10th Edition, 1983, pp. 508 and C188, item #3488.
The Condensed Chemical Dictionary, 10th Edition, 1981, p. 246.

Primary Examiner—Sidney Marantz
Assistant Examiner—William J. Herald
Attorney, Agent, or Firm—Schweitzer & Cornman

[57] ABSTRACT

The invention relates to a test strip for taking of daily blood sugar profiles, and also for glucose determination in urine for determining the individual kidney threshold of a diabetic as a daily profile, which finds use in glucose diagnosis.

The objective of the invention is to stabilize the test strip in its function and to adapt it to customary measuring instruments, and this is achieved by attaching a film reaction membrane to a carrier, wherein the membrane was post treated with a complexing agent and an acyclic hydroxyamine or amino derivative.

23 Claims, No Drawings

TEST STRIP FOR COLLECTING OF BLOOD SUGAR DAILY PROFILES AND PROCESS FOR ITS PREPARATION

SUMMARY OF THE INVENTION

The invention relates to a test strip for the collection of large or small blood sugar daily profiles under everyday conditions, which both before and after its use can be preserved under normal conditions, and can also be sent to other locations.

BACKGROUND AND PRIOR ART

Diabetes therapy is increasingly based on a normal glycemic considerations. This normoglycemic orientation requires a determination of the individual glycemic conditions under everyday conditions to control, and in a given case correct, nutrition adjustments and bodily activity for therapeutic purposes. Even today in excess of 50% of diabetics die from later damage which results from insufficiently stable normal glycemic metabolic conditions. Avoidance of such late damages, and where possible a remission to reach damage that has already taken place can be achieved only through a thorough lowering of glucose values in blood, to realize a stable normal glycemic condition.

Since the criteria for this adjustment are different for various individuals, and are influenced by the aforementioned factors, often the control by a physician of variations in the blood sugar value within a 24 hour day represents a significant consideration for the therapy and for the avoidance of latent effects.

Depending on the type of diabetic, small daily profiles with 5-6 determinations throughout the day, or large daily profiles with 11 determinations over a 24 hour period, for 1 to 12 week periods, are considered important.

Until now, this medical requirement in a limited manner can be 1. satisfied by saving of self-taken blood samples and by subsequent enzymatic laboratory analysis; or
2. the diabetic tests his blood sugar content with a special test strip developed for that purpose, which provides a semi-quantitative, visual, or respectively by using a reflection measuring apparatus for a quantitative determination.

According to method 1, the diabetic must pick up the blood sample with a capillary, and each capillary is a small tube containing a preservative liquid. An industrial testing tool set is prepared which is then to be sent to a laboratory where preparation and analysis are carried out. The preserved blood samples can be held for about 10 days. The method is demanding and is expensive and can be employed only in a limited manner.

A reflectometric evaluation is carried out with method 2, makes a quantitative method available, that has a sufficient accuracy. A documentation of the results is, nevertheless, not available, because the instability of the coloration. This deficiency compels immediate evaluation by the diabetic himself and requires the acquisition or ready availability of measuring apparatus for the evaluation of the testing strip.

Due to the limited number of blood sugar analytical methods, aside from the pregnant, juvenile or labile diabetics, which are between 5 and 11 blood sugar determinations per month, or respectively, per quarter, the conduct of the determinations are further burdened by a spread in the individual results due to a lack routine techniques. Therefore, the physician cannot arrive at estimates and the judgment of the values is made more difficult. The material requirements under these circumstances can be satisfied only in the case of juvenile or pregnant diabetics.

For the above reasons, a testing by the diabetics themselves by daily determinations and evaluation by a physician is considered to be an optimal method. In this manner it is possible to develop a blood sugar profile control for all diabetics under medical evaluation and control.

Recognizing the problems of the color instability of known test strips, developments were created to eliminate this deficiency by means of simple or multi-layer film carrier membranes that are prepared in various ways with gelatins, enzymes, indicators and additives. Even though color stability can be accomplished in this manner, there are considerable shortcomings with respect to adaptability to reflection measuring instruments, due to indicator function or the absorption spectrum. In addition, the reaction capability is strongly influenced by humidity, heat and light and this has prevented the use of these materials to date.

The layering of film carrier membranes that are known per se, with enzyme-indicator gelatins by adding wetting agents, softeners, color couplers and curing agents, shows a high spread in quatitative determination of blood sugar values, i.e. insufficient precision, which is conditioned through washing out effect of the indicator system, variations in haematocrit content variable subsequent hardening of the layer, through storage influences and variations in water uptake, i.e. swelling.

In the case of practical application, it is mainly the question to match the absorption spectrum and the indicator function to the available measuring instruments to obtain the required stability for its use.

It is known to treat enzyme-indicator gelatin layers subsequently with aequous solutions of chromium-III salts. By means of this post-treatment the wet strength should increase, in that the degree of wetting of the gelatins is changed. This post-treatment only changes the surface characteristics and has n effect on the functionality, the absorption spectrum and the stability.

Enzyme-indicator gelatin layers are also known for glucose determina,tion in which biphenyl derivatives are employed as chromogen with a fixing material, in which a reaction at a pH <5.0 results in a formation of a semiquinoneimine dye which will not wash out. Fixing and stability can be guaranteed absolutely only if when the liquid to be tested is not changed by this pH range, which, however, follows in the case of blood and sera having a pH around 7.0 and a action period effect of >30 seconds. For this reason the precision is sufficient only in aqueous acid solutions and the extinction values obtained, cannot be compared with blood and sera.

It is also known to apply two enzyme-indicator gelatine layers containing different enzyme concentrations, for the improvement of the functionality. As already explained above, also here when the fixing material is applied for stabilization at pH <5.0, the drawbacks of high spread, influence of haematocrits, and stability, are present without change.

The methods, test strips and layered membranes, respectively, all have the drawback that they cannot be adjusted to the reflection measuring apparati which are available in the trade for the last 10 years. The test strips that are now available are suitable only in a limited fashion for the determination of glucose daily profiles.

OBJECTIVE OF THE INVENTION

The objective of the invention is a test strip onto which a diabetic person applies a drop of blood. This is allowed to act on the strip for a period of time and is then wiped off and then sent to a physician for control and evaluation.

Each test strip should enable the notation of the time, date and name thereon. The desired stability should enable postal delivery and to guarantee accurate determination of glucose content.

The process for the preparation of the test strip is aimed at stabilizing the function of the film reaction membrane so that it maintains its properties constant for at least 4 weeks under normal storage conditions and after use the color reaction that took place is stable not only for evaluation within 4 weeks, but also remains stable thereafter for documentation purposes even for color comparison usable for visual evaluation in the case of single, in the meantime eventually corresponding determinations.

It is a further objective of the invention, to be able to adjust the function between glucose concentration and extinction as well as absorption spectrum so that an uncomplicated adaptation can be successfully carried out to available measuring instruments or to those that are available in the trade.

It is an objective to provide a simple process for the known enzymatic indicator reaction with glucose, without complicated multilayer structure, and without enzyme-conditioned differential reaction conditions or extremely low layer thickness, which process simply satisfies all the objectives.

It is a further objective to develop the process for the test strip that by the aid of differential calibration strips two to three various measurement ranges should be available for predetermined therapeutic range controls with the same test strip.

COMPLETE DISCLOSURE OF THE INVENTION

It is a task of the invention to obtain the conditions and requirements necessary for the determination of blood sugar daily profiles, including stability of the test strip, stability of the coloration, precision of the results, adaptability to reflection measuring apparatus available in the trade, and adjustabiity to various measuring ranges, without complicated multilayer reaction conditions or especially thin layering and without the consequential functional and absorption spectrum drawbacks.

It is a task of the invention to alter by a post treatment the function of the known types of enzyme-indicator gelatine layers by means of a simple, technically uncomplicated process, to increase its water absorption capability in 1 minute by 10 to 25%, a visually different color reaction takes place which, instead of the radiant blue, acid-fixed dye results in the formation of a grey to blue-grey color which can be measured at 610 to 625 nm, and at the same time increases precision, decreases haematocrit dependency, and results in the achievement of a stability that permits the mailing of the test strip and the profile values.

For the solution of this task an about 20μ strong enzyme-indicator gelatine layer is applied to a carrier membrane or foil in a known manner. The layer corresponds to an enzyme-indicator ratio that is known for over 20 years, and which can contain softeners, wetting agents, crosslinking agents or dye couplers that are normally known from the photographic industry for gelatin layers. These are applied to a carrier membrane and then dried in a manner known per se.

According to the invention, the dried film membrane that has a layer applied to it, is conducted through a 0.01 to 0.1 molar complexing agent, preferably Komplexon I which is nitriloacetic acid or ethylenediamine tetraacetic acid (EDTA), for a period of 5 to 30 seconds, and then for 60 to 120 seconds through an acyclic hydroxyamine or amino derivative containing 0.01 to 1 molar, preferably 0.02 to 0.5 molar solution. For example choline or amino-trishydroxy-methyl-methane is suitable as the acyclic hydroxyamine, and collidin, quinoline or piperazin is suitable as the amino derivative.

It is, however, also possible to treat the layered film membrane in a single solution instead of two successive ones. The layer that is treated in that manner satisfies the requirements for a receiving medium for blood sugar daily profiles and can be adapted to all reflection measuring devices that are available in the trade.

Colorless, or monochrome colored plastic membranes that are insoluble in water can be used as a carrier for the reaction layer.

The layering of the film membranes can be applied over the entire surface of the carrier, or only partially, in any technically possible width, according to purpose of application or economic utilization.

Suitably a white membrane or foil is used as the carrier for the evaluation of the layered film-carrying membranes on a reflection photometer.

A universal solution is obtained when a transparent, coated film membrane is partially connected to a white carrier cardboard by sealing or adhesion so that thereby the reflection as well as transparency measurements can be carried out on the same test strip. Adhesive tape, or adhesive layered PVC, polyester, cellulose acetate or other membranes can be employed. Test strips that are produced in that manner can carry preprinted spaces for name, date, time of day to avoid any confusion.

Film membranes that have a layer applied to them in the above manner, can also be used for the quantitative determination of glucose in urine, and can be in the same manner, except for changing the reaction time, used for the determination of blood sugar, on the available apparatus. Thus it is possible to determine the individual kidney threshold value for diabetics as a daily profile, whereby daily control can be made individually more precise by semiquantitative test strips.

It was found that it is particularly advantageous for this purpose to connect the film reaction membrane prepared in accordance with the process of the present invention, to filter paper by adhesion or by sealing, and it was shown that the layered side should overlay the filter paper.

A colorless membrane is used for the adhesion, which does not distort the measured results, e.g. a polyester- or cellulose acetate membrane provided with an adhesive layer. The layered film membrane can be cut into 5 to 10 cm wide strips and the strip it attached at one or preferable at both ends onto the carrier.

When the carrier is immersed, the filter paper transfers the absorbed liquid onto the reaction layer and at the same time acts as a means for determining the dosage, since the excess of the liquid to be tested, will migrate onward in the strip.

The test strip prepared in accordance with the method of this invention, delivers color stable colorations which correspond to the instantaneous glucose content and which can be preserved for documentation, which can be evaluated at a desired time by the diabetic or a physician or a laboratory.

The test strip is prepared in accordance with the process of the invention, so that it is sufficiently storable at room temperature and can be mailed by the physician to the diabetic and, after its use by the diabetic, returned by mail to the physician, without any distortion of the obtainable results.

The test strip prepared in accordance with the invention can be evaluated in transmitted light and can also be adjusted for reflection measuring instruments. The color formation and the increase in extinction can be adjusted according to the process of the invention, so that two measuring ranges can be encompassed within the same partial strip, by means of two calibrating strips, thus to increase the precision of the results.

It is possible to adjust a measuring range, preferably for juvenile and for pregnant diabetics, which corresponds mainly to the hypoglycemic to mildly hypoglycemic range, or the measuring range with its center of gravity extending between the normoto hyperglycemic.

The test strip thus solves the requirements of controlled therapy for all forms of diabetes and of a universal evaluation and utilization.

EXAMPLES

Example 1

A 7% gelatin solution which contains in 100 ml 2000 U (unit) POD which is enzyme peroxidase, and U (unit) GOD which is enzyme gluocose oxidase and 8000 U (unit) POD which is enzyme peroxidase, and U (unit) GOD which is enzyme glucose oxidase, 0.3 g 0-tolidine as well as 0.45 of a naphthol derivative as coupler and additionally crosslinking agents and softeners, is reacted with a hardener, such as a chromium III salt, before application of the layer. With this solution an about 20μ thick layer is applied to a film membrane, and is then dried.

In an immersion process the layer is swelled for 10 seconds by a 0.01 molar EDTA solution, excess liquid is removed and immediately thereafter the path of the film is led through a second immersion bath which contains 0.05 mol collidine in which the layer is post-treated, i.e. further swelled for 90 seconds. Subsequently the swollen, post-treated layer is dried in a known manner.

Example 2

In other embodiments according to Example 1, instead of collidine,
piperazin in a 0.03 molar solution
cholin in a 0.04 molar solution
amino-trishydroxymethyl-methane in a 0.02 molar solution
is employed for the aftertreatment in the above manner.

Example 3

In a different embodiment, analogously to Example 1, the swelling and post treatment are carried out in a single solution. For this 0.01 mol EDTA and 0.05 mol amino-trishydroxymethylmethane are dissolved in 1000 ml water and the reaction film layer is swelled and, respectively post-treated for 80 seconds in this solution.

Example 4

In a different embodiment, according to Example 1, 0.01% Pinaverdol which is a trademark for an isocyanin dye sold by Hoechst is added to the post-treatment solution, whereby the reaction layer is given a weak red-violet coloration without disturbing later measurements and results.

Example 5

One proceeds in accordance with Example 1. The layered film membrane, with the reaction layer facing upward, and the film membrane toward a carrier, is sealed to a white cardboard carrier.

Example 6

One proceeds according to Example 1. The layered film membrane is glued at both ends, by means of an adhesive tape, with the reaction layer facing the carrier, onto white filter paper, whereby the adhesive tape completely covers the film membrane and the carrier only to an extent of about 5 mm.

Example 7

One works in accordance with Example 1. An artwork printing cardboard is used with a gelatin coating. A film reaction membrane which is coated on its backside with gelatin, is used. The connection between the film reaction membrane and carrier cardboard follows at one end with an aqueous adhesive.

We claim:
1. A test strip for receiving blood sugar daily profiles, comprising a carrier, a film forming membrane, and an enzyme indicator reaction layer disposed on said membrane, said reaction layer containing glucose oxidase, peroxidase, and o-tolidine, said reaction layer being treated with from about 0.01 to about 0.1 mole of a chelating agent and with from about 0.01 to about 1 mole of choline, amino-trihydroxymethylmethane, collidine, quinoline or quinoazine.

2. The test strip according to claim 1, characterized in that the film membrane is made from a plastic membrane that is insoluble in water.

3. The test strip according to claim 2, characterized in that the plastic membrane is colorless, white or colored.

4. The test strip according to claim 1, characterized in that the surface of the film membrane is entirely or only partly coated with the reaction layer.

5. The test strip according to claim 1, characterized in that the carrier is made from white plastic membrane.

6. The test strip according to claim 1, characterized in that the carrier is white filter paper.

7. The test strip according to claim 1, characterized in that the film reaction membrane is connected to the carrier by sealing or by adhesion.

8. The test strip according to claim 1, characterized in that the film reaction membrane is partially or totally connected to the carrier.

9. The test strip according to claim 1, characterized in that the film reaction membrane is connected to the carrier with a polyvinyl chloride polyester or cellulose acetate foil having a layer of adhesive thereon which does not affect the measurement function.

10. The test strip according to claim 1, wherein the reaction layer of the film reaction membrane which is facing the carrier, is connected to filter paper.

11. The test strip of claim 1, wherein the membrane further contains a softener, crosslinking agent, and a dye coupler, or a softener and crosslinking agent, or a dye coupler.

12. Test strip according to claim 1, wherein the carrier substrate is a white cardboard.

13. A method for determining glucose in urine specimen, comprising applying the urine specimen of a diabetic to the test strip of claim 1, and observing the result.

14. A process for preparing a test strip for receiving blood sugar daily profiles, comprising a carrier, a film forming membrane, and an enzyme indicator reaction layer disposed on said film forming membrane, said enzyme indicator reaction layer containing glucose oxidase, peroxidase, and o-tolidine, the process comprising the steps of:
(a) applying the film forming membrane to the enzyme indicator reaction layer,
(b) swelling the indicator reaction layer with from about 0.01 to about 0.1 mole of a chelating agent and from 0.01 to about 1 mole of choline, amino-trishydroxymethylmethane, collidine, quinoline, or piperazin,
(c) treating the reaction layer with additional amounts of said chelating agent and choline, amino-trishydroxymethylmethane, collidine, quinoline or piperazin, and
(d) applying the layered film forming membrane to the carrier.

15. A process according to claim 14, wherein the complexing agent is permitted to act for a period of 5 to 30 seconds.

16. A process according to claim 14, wherein nitriloacetic acid is used as the complexing agent.

17. A process according to claim 14, wherein EDTA is used as the complexing agent.

18. A process according to claim 14, wherein the choline, amino-trishydroxymethylmethane, collidine, quinoline, or piperazin is used in a 0.02 to 0.5 molar concentration.

19. A process according to claim 14, wherein the choline, amino-trishydroxymethylmethane, collidine, quinoline, or piperazin is permitted to act for a period of 60 to 120 seconds.

20. A process according to claim 14, wherein the film reaction membrane is simultaneously treated with a complexing agent and an choline, amino-trishydroxymethylmethane, collidine, quinoline, or piperazin.

21. A process according to claim 14, wherein the water absorption capacity of the film reaction membrane is increased by 10 to 25% per minute as a result of treating it with the chelating agent and choline, amino-trishydroxymethylmethane, collidine, quinoline, or piperazin.

22. A process according to claim 14, wherein the complexing agent is permitted to act for a period of about 5 to about 10 seconds.

23. The process of claim 14, wherein the membrane further contains a softener, crosslinking agent, and a dye coupler, or a softener and crosslinking agent, or a dye coupler.

* * * * *